United States Patent
Wu et al.

(10) Patent No.: US 11,648,224 B2
(45) Date of Patent: May 16, 2023

(54) USE AND METHOD OF L-ASPARTIC ACID BETA-HYDROXAMATE IN PREPARING DRUGS FOR INHIBITING CHOROIDAL NEOVASCULARIZATION

(71) Applicant: WENZHOU MEDICAL UNIVERSITY, Wenzhou (CN)

(72) Inventors: Shengzhou Wu, Wenzhou (CN); Mengjuan Wu, Wenzhou (CN); Yimei Liu, Wenzhou (CN)

(73) Assignee: WENZHOU MEDICAL UNIVERSITY, Wenzhou (CN)

( * ) Notice: Subject to any disclaimer, the term of this patent is extended or adjusted under 35 U.S.C. 154(b) by 198 days.

(21) Appl. No.: 17/373,284

(22) Filed: Jul. 12, 2021

(65) Prior Publication Data
US 2021/0338620 A1   Nov. 4, 2021

Related U.S. Application Data

(62) Division of application No. 16/438,670, filed on Jun. 12, 2019, now abandoned.

(30) Foreign Application Priority Data

Feb. 20, 2019   (CN) .......................... 201910125597.5

(51) Int. Cl.
*A61K 31/198*   (2006.01)
*A61P 27/02*   (2006.01)
*A61K 9/00*   (2006.01)

(52) U.S. Cl.
CPC .......... *A61K 31/198* (2013.01); *A61K 9/0019* (2013.01); *A61P 27/02* (2018.01)

(58) Field of Classification Search
CPC ................................................... A61K 31/198
See application file for complete search history.

(56) References Cited

U.S. PATENT DOCUMENTS 5,571,839 A * 11/1996 Vila ....................... A61K 38/50
                                                                       514/564

* cited by examiner

*Primary Examiner* — Yong S. Chong
(74) *Attorney, Agent, or Firm* — Christensen, Fonder, Dardi & Herbert PLLC

(57) ABSTRACT

A method of inhibiting or treating choroidal neovascularization, wherein the method comprises administering an injectable preparation of L-aspartic acid β-hydroxamate to a patient suffering from choroidal neovascularization, including injecting a first dosage that is 6 mg/kg by weight of the treated subject, and injecting a second dosage that is 3 mg/kg.

3 Claims, 21 Drawing Sheets
(12 of 21 Drawing Sheet(s) Filed in Color)

USE AND METHOD OF L-ASPARTIC ACID BETA-HYDROXAMATE IN PREPARING DRUGS FOR INHIBITING CHOROIDAL NEOVASCULARIZATION

PRIORITY CLAIM

The present application is a divisional of U.S. patent application Ser. No. 16/438,670, filed on Jun. 12, 2019, which claims priority to Chinese Patent Application No. 201910125597.5, filed on Feb. 20, 2019, which said applications are incorporated by reference in their entirety herein.

TECHNICAL FIELD

The present invention particularly pertains to the technical field of choroidal neovascularization, and specifically pertains to a use and method of L-aspartic acid 3-hydroxamate in preparing drugs for inhibiting choroidal neovascularization.

BACKGROUND

Choroidal neovascularization (CNV) is an important pathological feature of exudative age-related macular degeneration (exAMD), which is the primary cause of visual loss in age-related macular degeneration (AMD). Currently, anti-VEGF antibodies (including bevacizumab, ranibizumab, etc.) are widely used in clinic, while there would be severe side effects after repeated intravitreal injections of anti-VEGF antibodies, including retinal and choroidal atrophy caused by long-term use of VEGF antibodies, retinal detachment and intraocular infection induced by repeated intravitreal injections, thus it would be an urgent need for better therapeutic regimens.

SUMMARY

To avoid the defects in the prior art, the present invention provides a use and method of L-aspartic acid β-hydroxamate in preparing drugs for inhibiting choroidal neovascularization, which, by inhibiting RPE from producing VEGF and MCP-1 which was induced with inflammation mediators, thus plays a role of inhibiting CNV in laser-damaged animal models.

The technical solution employed in the present invention is: a use of L-aspartic acid β-hydroxamate in preparing drugs for inhibiting choroidal neovascularization.

The use of L-aspartic acid β-hydroxamate in preparing intravenous drugs for inhibiting choroidal neovascularization.

The first dosage of L-aspartic acid β-hydroxamate in the intravenous drugs for inhibiting choroidal neovascularization is 6 mg/kg by weight of the treated subject, and the second dosage is 3 mg/kg.

The method is by means of injecting L-aspartic acid β-hydroxamate, the first dosage injected is 6 mg/kg by weight of the treated subject, and the second dosage is 3 mg/kg.

The injection is by means of intravenous injection.

The second dosage is to inject 3 mg/kg of L-aspartic acid β-hydroxamate for the second time by weight of the treated subject, after 3 days of the first injection of L-aspartic acid β-hydroxamate.

The present invention has the following benefits: the present invention provides a use and method of L-aspartic acid β-hydroxamate in preparing drugs for inhibiting choroidal neovascularization, which inhibits the production of VEG and MCP-1 mediated by RPE which was induced with TNFα by intravenously injecting L-aspartic acid β-hydroxamate, thus having an effect of inhibiting choroidal neovascularization, and there would not be severe side effects, including retinal and choroidal atrophy, retinal detachment and intraocular infection caused by repeated intravitreal injections of anti-VEGF antibodies.

BRIEF DESCRIPTION OF THE DRAWINGS

The patent application contains at least one drawing executed in color. Copies of this patent with color drawings will be provided by the Patent and Trademark Office upon request and payment of the necessary fee.

DETAILED DESCRIPTION OF THE EMBODIMENTS

Experimental Methods

Using animal models of exAMD, in C57/B6 mice, fundus was irradiated with Krypton red laser (interval at 0.05 s, duration of 0.07 s, and power at 240 mW) to make CNV mice models. A serine racemase competitive inhibitor, L-aspartic acid β-hydroxamate (L-ABH), was injected intravenously at a dosage of 6 mg/kg at the day before laser, and at a dosage of 3 mg/kg at the third day after laser. At the seventh day after laser injury, stretched preparation was performed with choroid/retinal pigment epithelial cells (RPEs), which were stained with metaagglutinin GS-IB4 coupled with Alexa Fluor 594, and the volume of CNV was analyzed. And primary RPEs were utilized in vitro to study the inhibition of L-ABH on the production of VEGF and MCP-1 by RPEs which was induced with TNFα. Macrophages were co-cultured with RPEs to study L-ABH about pre-treating RPEs and inhibiting the migration of macrophages.

Figure 1A:
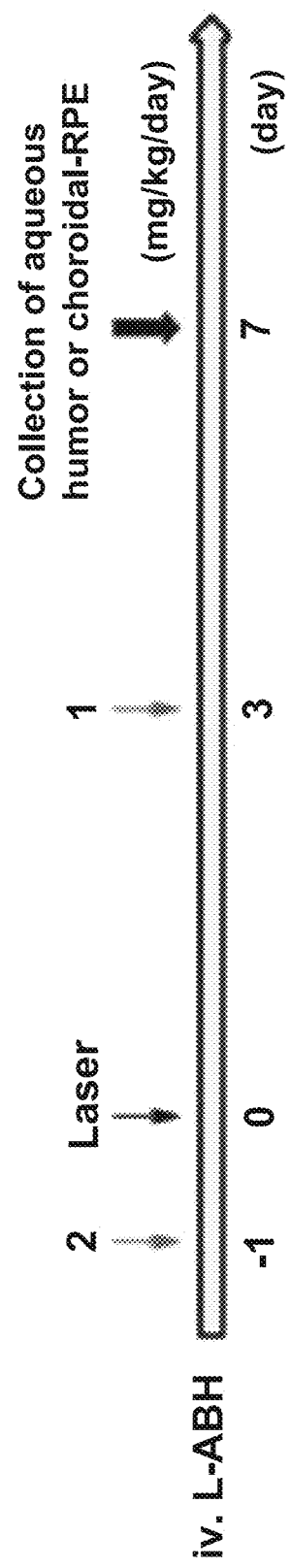
FIGS. 1A-1G are schematic diagrams depicting results of inhibiting the laser-induced choroidal neovascularization by intravenously injecting the L-ABH of the present invention.
Figure 1B:
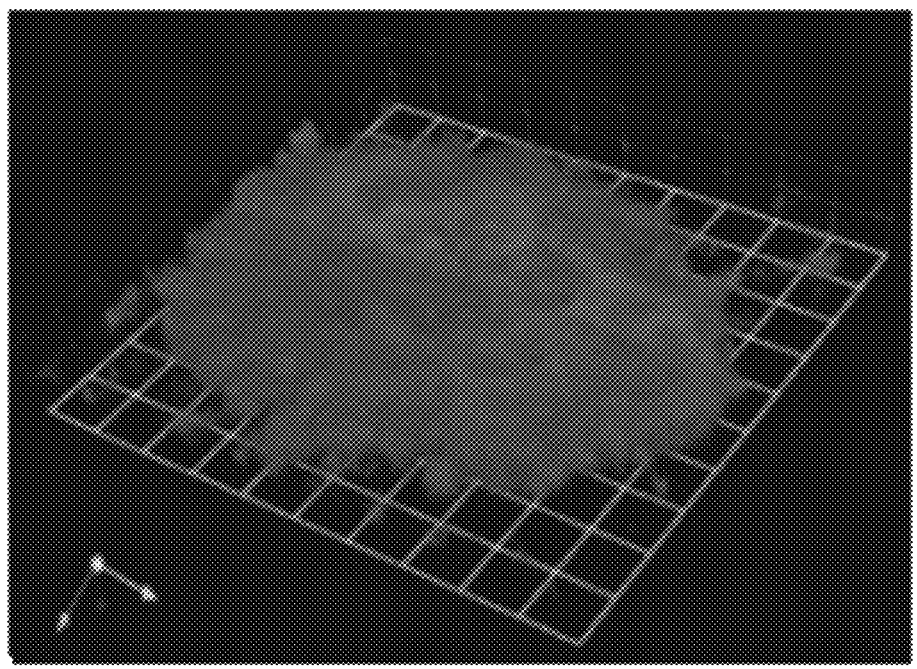
Figure 1C:
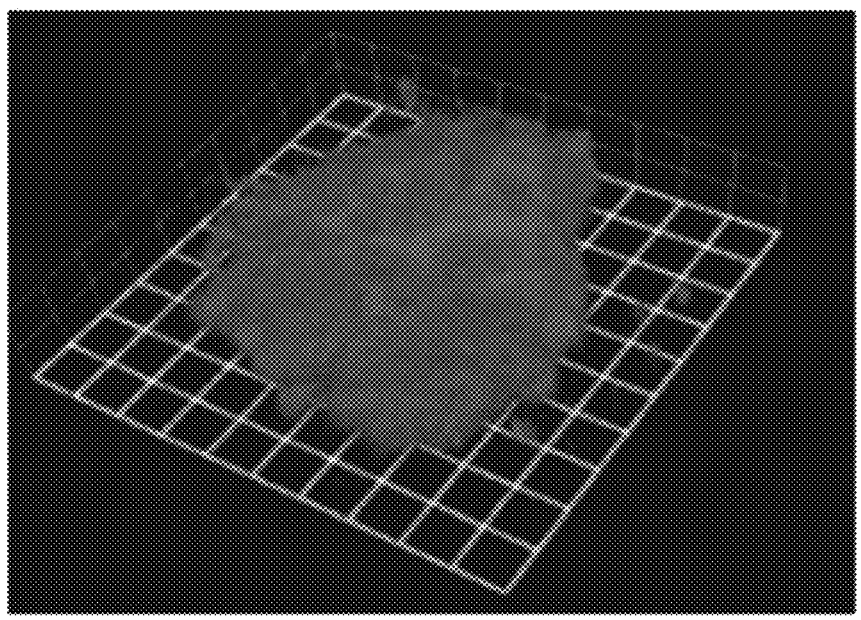
Figure 1D:
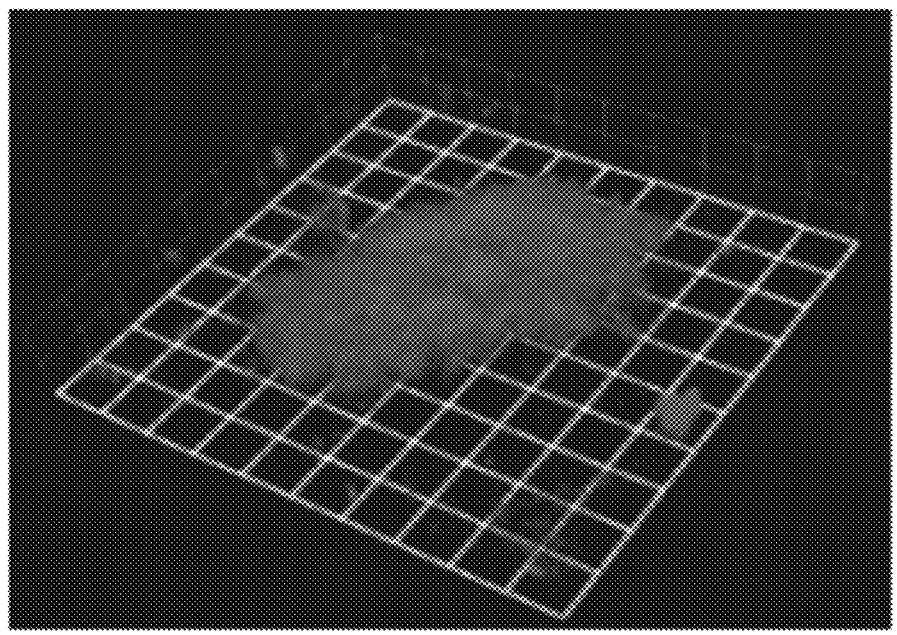
Figure 1E:
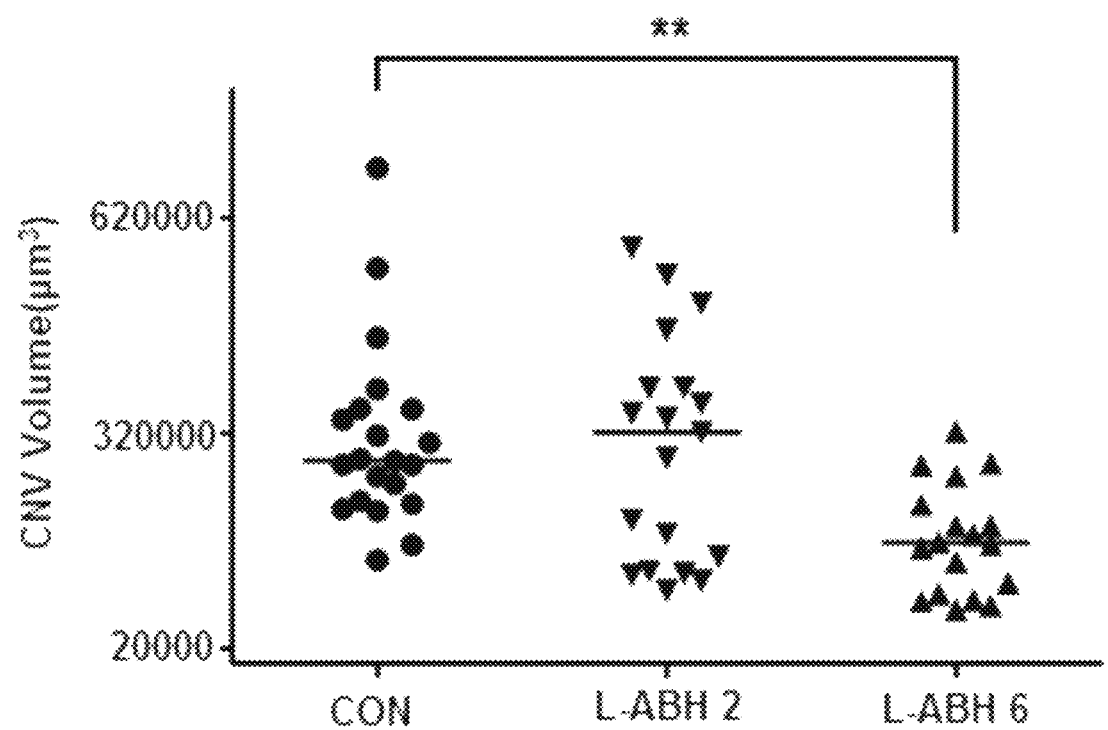
Figure 1F:
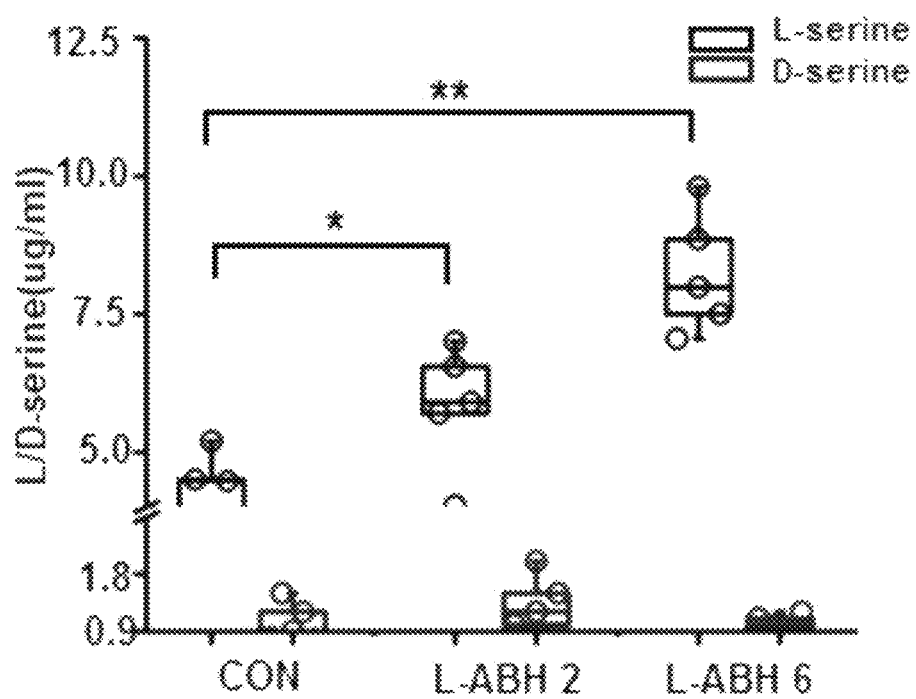
Figure 1G:
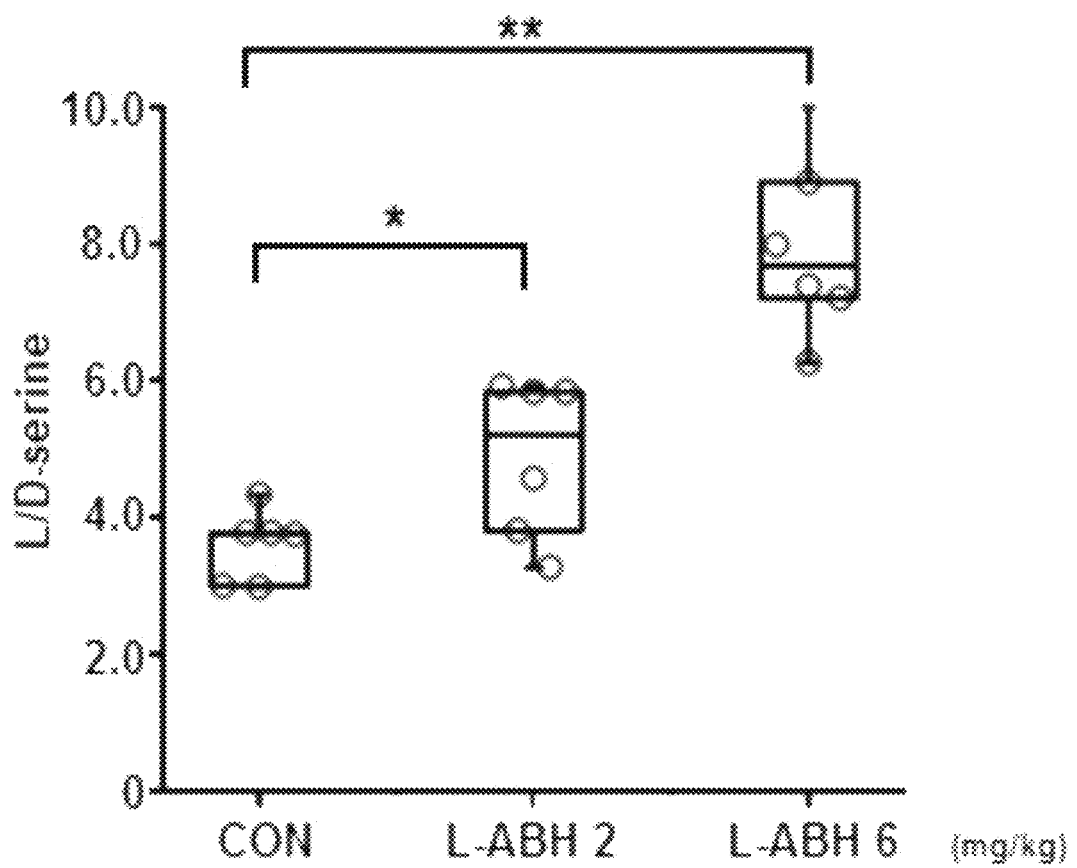

The results of inhibiting the laser-induced choroidal neovascularization by intravenously injecting L-ABH are shown in FIGS. 1A-1E, wherein FIG. 1A is CNV produced by laser in 2-month-old wild-type mice. Injection of saline was used as the control group (Con, B); at the day before laser, L-ABH was injected intravenously (2 mg/kg), and 1 mg/kg (C) was injected 3 days after laser; or at the day before laser, L-ABH was injected intravenously (6 mg/kg), and 3 mg/kg (D) was injected 3 days after laser. At the 7th day after laser, stretched preparation was performed with choroid, which was stained with metaagglutinin, and photographed confocally by laser. FIG. 1B is the control group (n=35 mice); FIG. 1C is the group with an initial injection of 2 mg/kg L-ABH (n=15); FIG. 1D is the group with an initial injection of 6 mg/kg L-ABH (n=20), **p<0.01. FIG. 1E is the scatter diagram of statistical results on the CNV volumes of each group. FIG. 1F is the contents of L, D-serine in the aqueous humor of mice in the control group and two treatment groups, and FIG. 1G is the analysis on the ratio of L/D-serine, *p<0.05, **p<0.01.

Figure 2A:
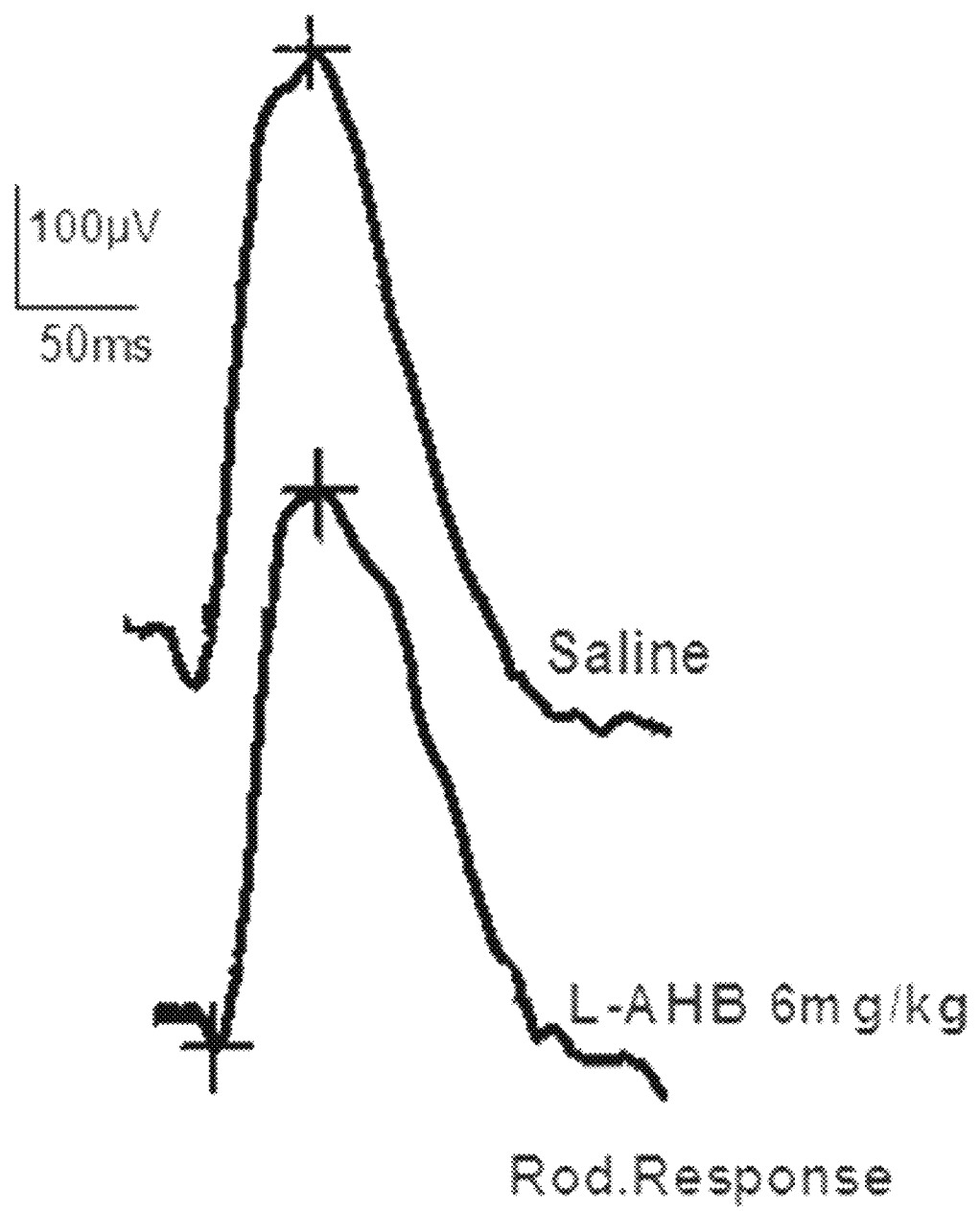
FIGS. 2A-2D are schematic diagrams depicting results of the effects on the retinal functions by intravenous injection of the L-ABH of the present invention.
Figure 2B:
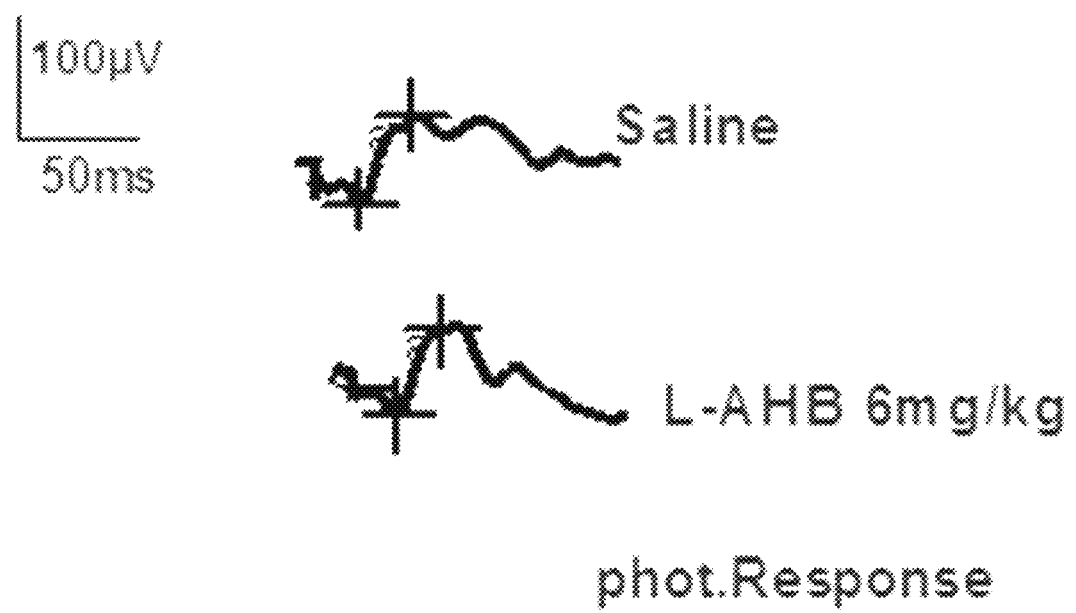
Figure 2C:
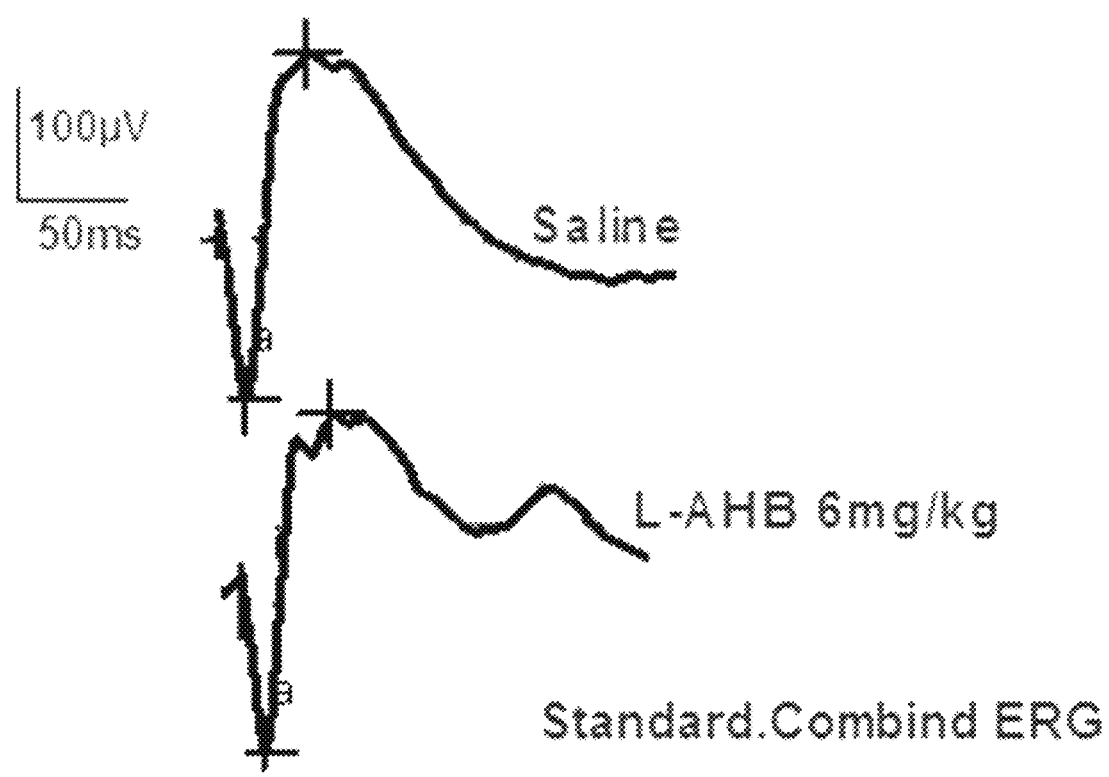
Figure 2D:
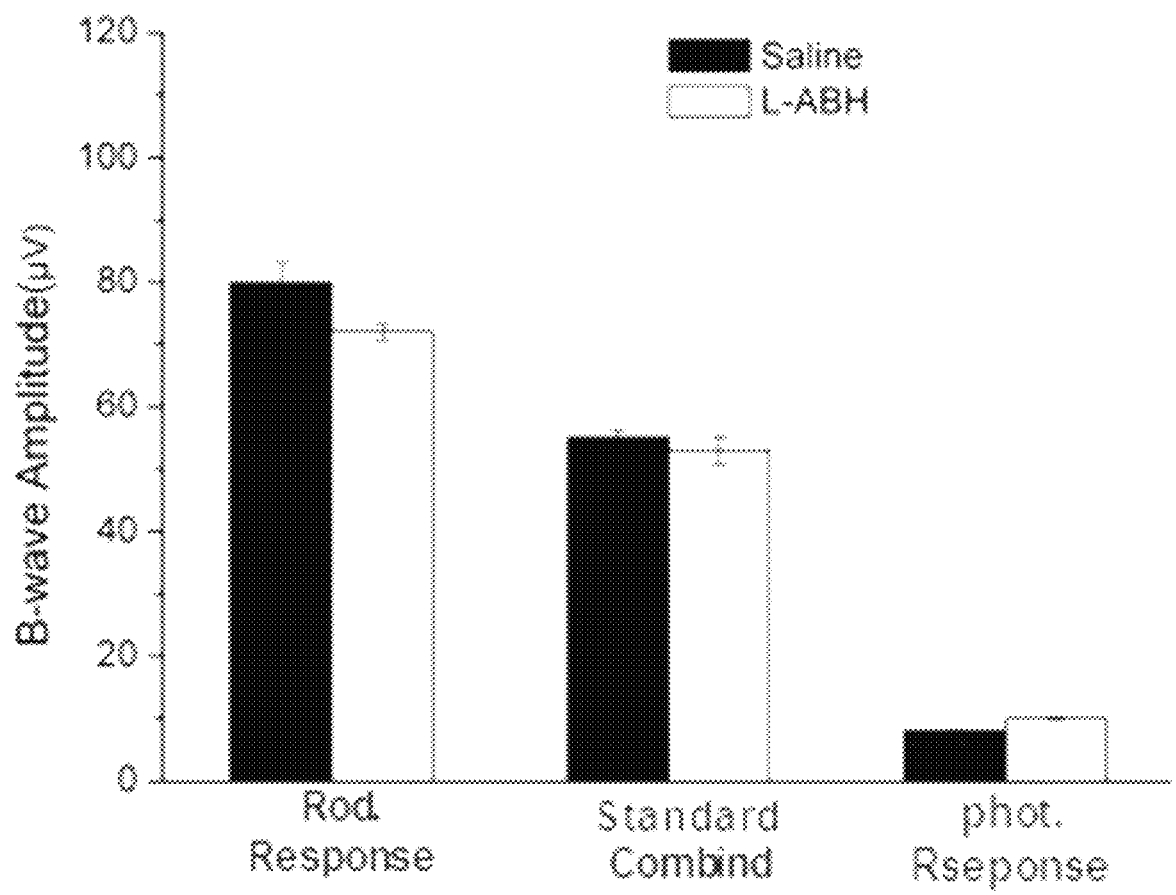

The effect of intravenous injection of L-ABH on retinal functions is shown in FIGS. 2A-2D, in which C57BL/6J male mice were intravenously injected 6 mg/kg of L-ABH at an age of two months, one day after the injection, an electrographic analysis was performed on the retina. The amplitudes of B-wave in dark and bright views are shown in FIG. 2A, FIG. 2C, and FIG. 2B respectively, and the average values of which are analyzed by histograms in FIG. 2D. The amplitude of B-wave originally from rod cells in a dark view for the control group and the L-ABH injection group, and the amplitude of B-wave originally from cone cells in a bright view have no differences compared with the saline injection group, indicating that there was no effect of intravenous injection of L-ABH on retinal functions.

Figure 3A:
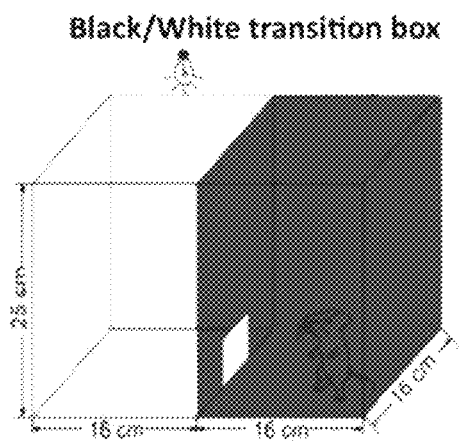
FIGS. 3A-3C are schematic diagrams depicting the results of the effects on the visual functions by intravenous injection of the L-ABH of the present invention.
Figure 3B:
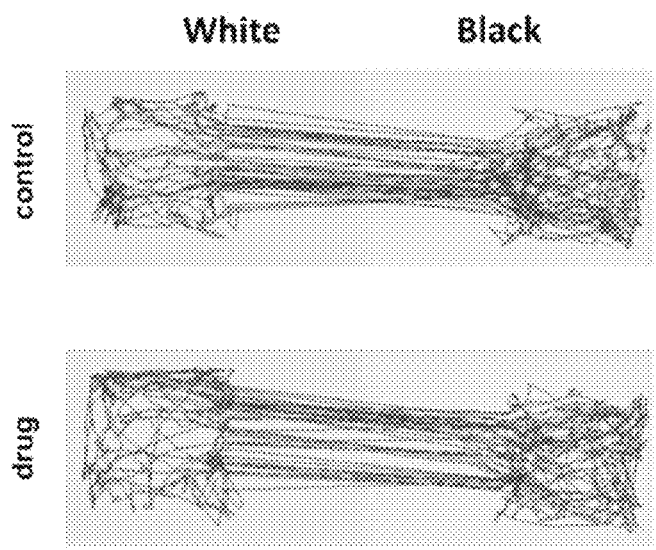
Figure 3C:
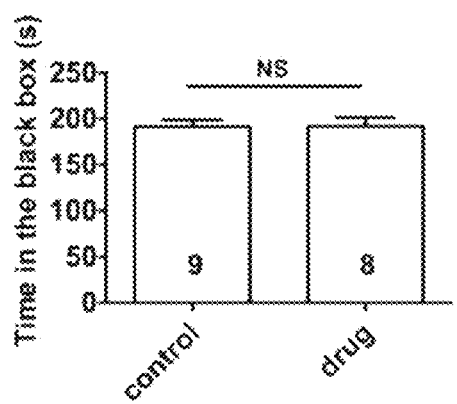

The effect of intravenous injection of L-ABH on visual functions are shown in FIGS. 3A-3C, in which C57BL/6j male mice were intravenously injected 6 mg/kg of L-ABH at an age of two months, one day after the injection, visual behaviors were analyzed. FIG. 3A, shows a black/white box, between which there was a small hole providing a free access for mice. FIG. 3B, shows the motion tracks of mice of the control group and the L-ABH (drug) group in the black/white box. FIG. 3C, shows the retention time of mice of the control group and the L-ABH (drug) group in the black box, showing no difference, indicating that there was no effect of intravenous injection of L-ABH on visual functions.

Figure 4A:
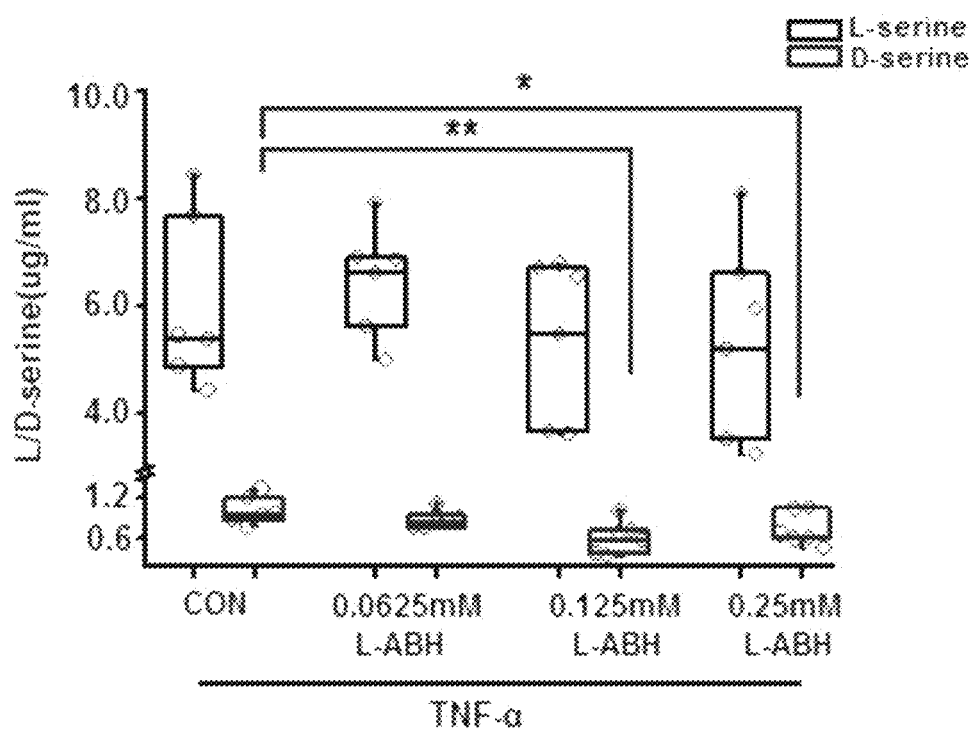
FIGS. 4A-4E are schematic diagrams depicting results of inhibiting the production of VEGF and MCP-1 by RPE which was induced with TNFα, by the L-ABH of the present invention.
Figure 4B:
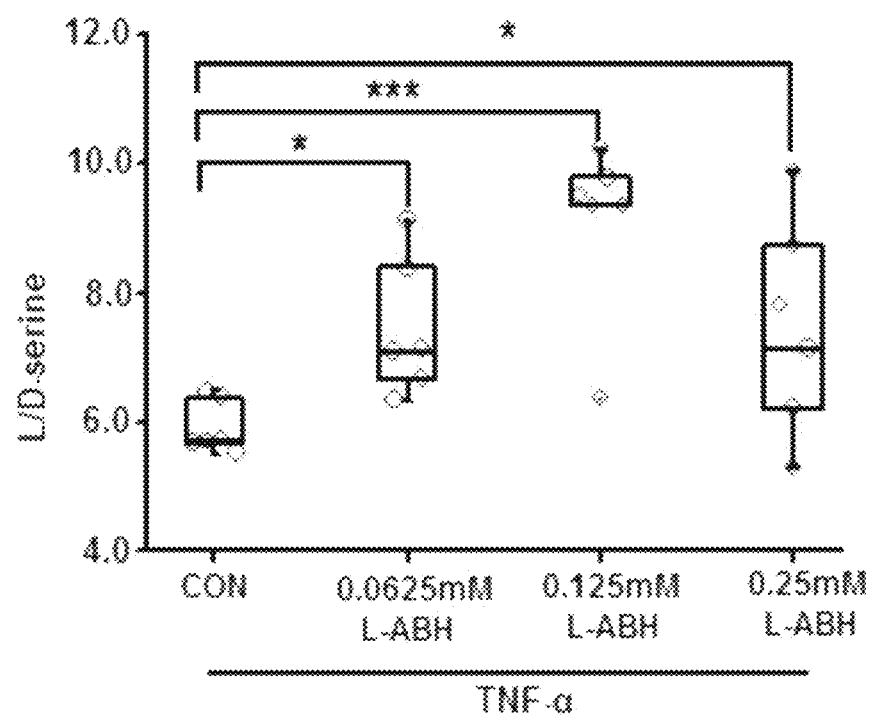
Figure 4C:
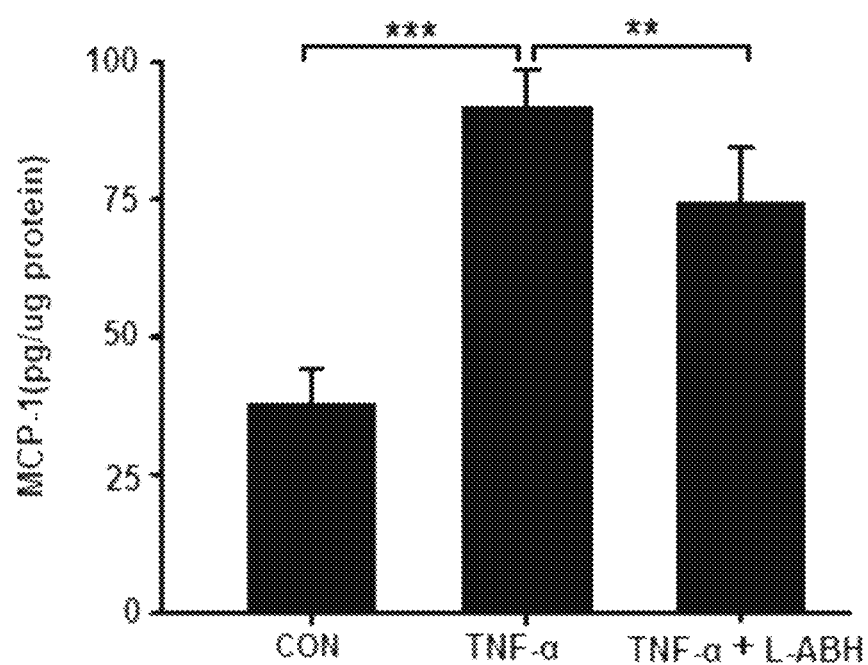
Figure 4D:
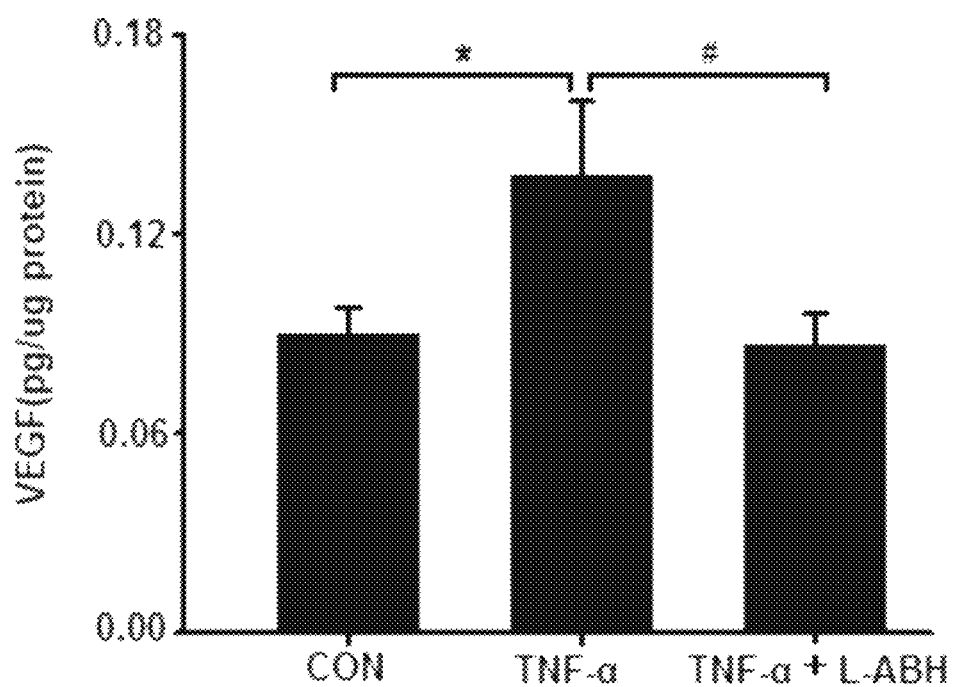
Figure 4E:
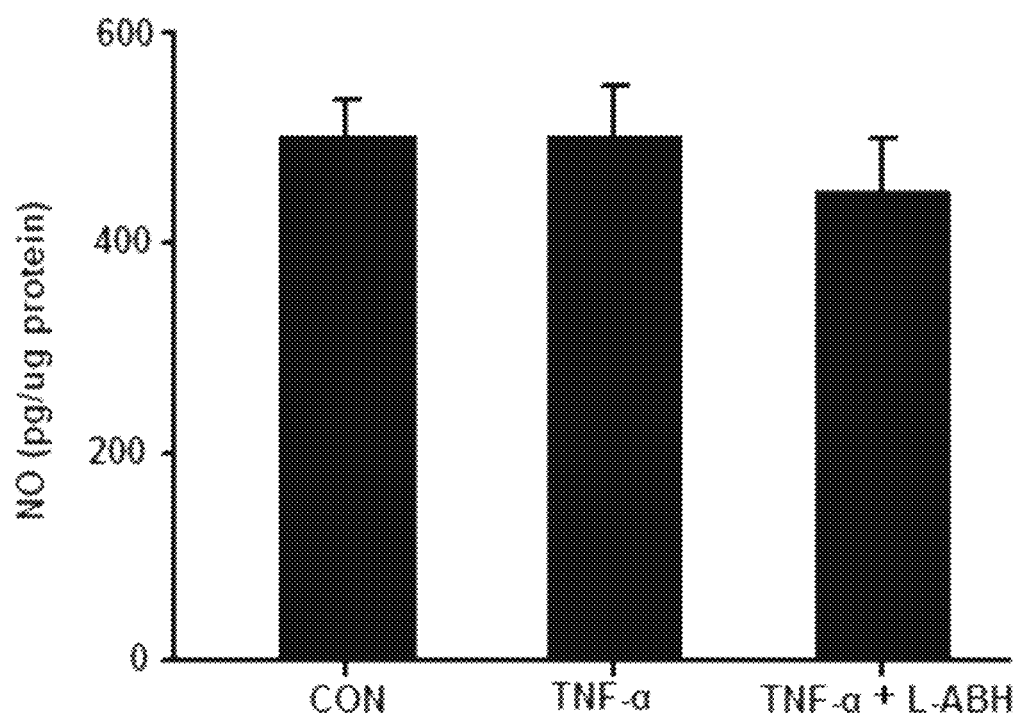

The experimental results of L-ABH inhibiting the production of VEGF and MCP-1 by RPE which was induced with TNFα are shown in FIGS. 4A-4E, wherein in FIG. 4A-FIG. 4B, L-ABH decreased the production of D-serine in primary RPEs, while increased the ratio of L-serine/D-serine. Primary RPE was cultured in DMEM/F12 plus 20% FBS to a density of 70%, at which it was exchanged for DMEM/F12 plus 1% FBS, L-ABH (0.0625-0.25 mM), or after the control pre-treatment for 1.5 hours, it was exchanged for TNFα (500 unit/ml) to treat for 12 h, the supernatants were collected, and L-serine and D-serine in the supernatants were detected by high performance liquid chromatography. There were six samples in each group. The contents of L-serine and D-serine are shown with box charts in FIG. 4A, with **p<0.01, *p<0.05 showing that there was significant difference of D-serine between the treatment group and the control group. The ratio of L/D-serine was shown in FIG. 4B, with **p<0.01, *p<0.05 showing that there was significant difference between the control groups. In FIG. 4C—FIG. 4E, primary RPEs were co-cultured with macrophages J774A.1, primary RPEs were pretreated with L-ABH (0.125 mM) for 1.5 h, then treated with TNFα (500 unit/ml) for 12 h, with J774A.1 being cultured in the upper layer at the same time for 12 h, after which the supernatants cultured with RPEs were collected, and an enzyme-linked immunosorbent assay was used to detect the productions of MCP-1 (C), VEGF (D), and NO (E). (There were 7 samples for each group). In FIG. 4C, *p<0.001, compared with the control group, p<0.01, compared with TNFα treatment group. In FIG. 4D, *p<0.05, compared with the control group, #p<0.05, compared with TNFα treatment group.

Figure 5A:
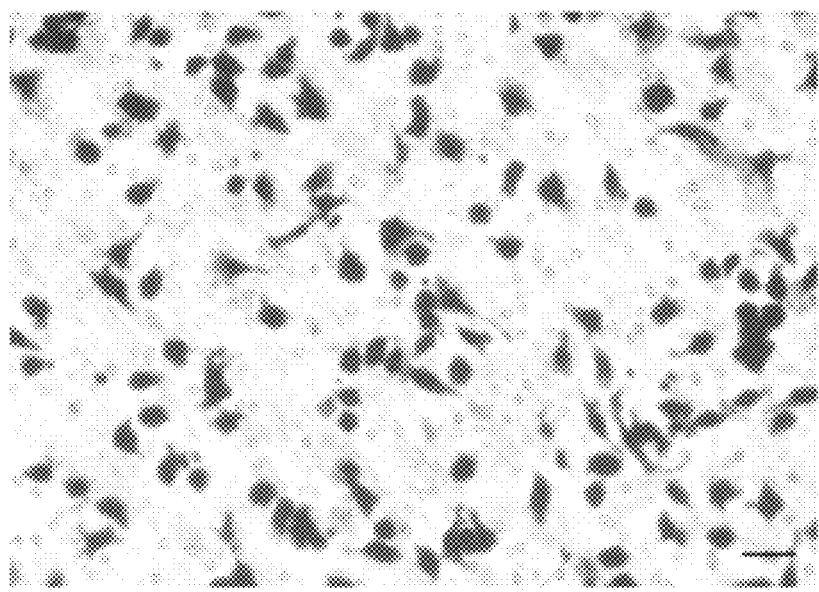
FIGS. 5A-5D are schematic diagrams depicting results of inhibiting the migration of macrophages under the induction of RPE treated with TNFα, by the L-ABH of the present invention.
Figure 5B:
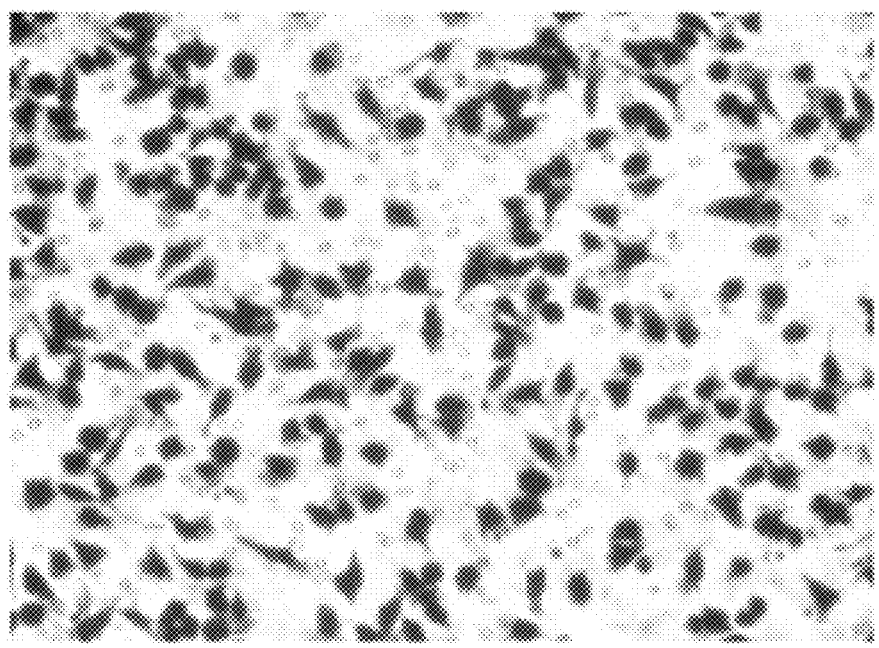
Figure 5C:
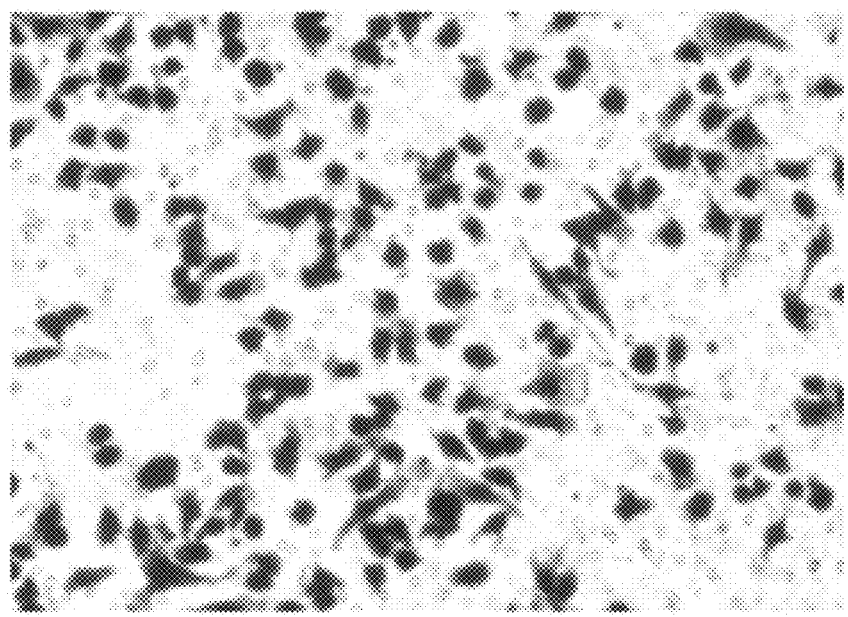
Figure 5D:
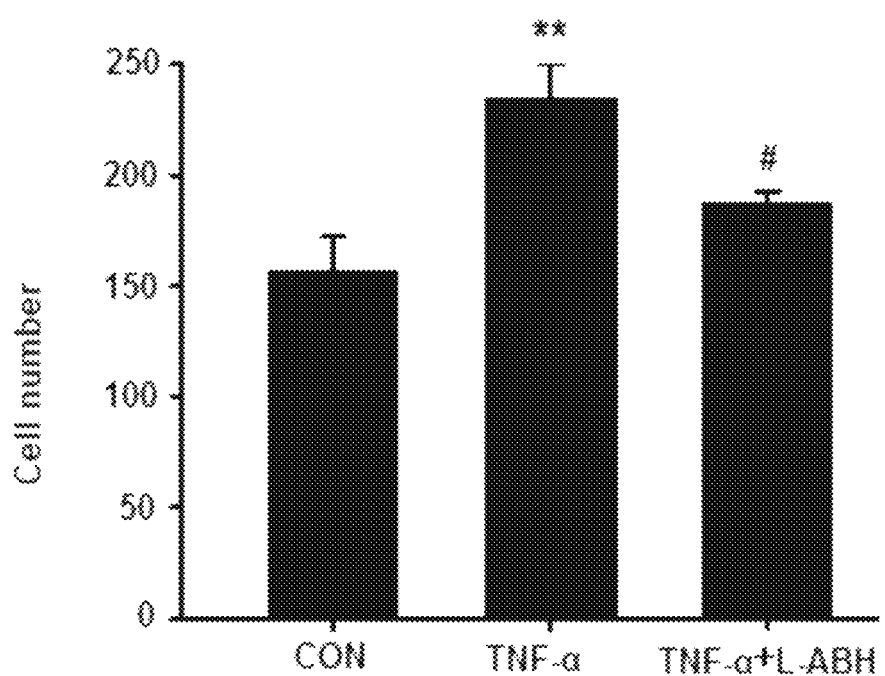

The results of L-ABH inhibiting the migration of macrophages under the induction of RPE treated with TNFα are shown in FIGS. 5A-5D, in which RPE was co-cultured with macrophages J774A.1 for 12 h. Treatments on RPE were divided into 3 groups, the control group (FIG. 5A), treatment with TNFα (500 unit/ml) for 12 h (FIG. 5B), pre-treatment with L-ABH (0.125 mM) for 1.5 h, then treatment with TNFα for 12 h (TNFα+L-ABH) (FIG. 5C). There were 7 samples for each group. The non-transmembrane cells were wiped off with cotton swab sticks, and the transmembrane macrophages were stained with crystal violet. For each culture dish, nine visual fields were randomly selected under the light microscope to be counted, with the statistical analysis seen in FIG. 5D. **p<0.01, compared with the control group, #p<0.05, compared with TNFα treatment group.

Experimental Results

We found that L-ABH reduced the volume of CNV significantly (the control group of 55% saline, p=0.001, 10 mice for each group). There would not be negative effects on the retinal functions and visual behaviors by injection of L-ABH. To study the mechanism, the primarily cultured RPEs were pre-treated with L-ABH, significantly decreasing the production of vascular endothelial growth factor (VEGF) and macrophage chemotactic protein-1 (MCP-1) by RPE which was induced with TNFα. Consistent with these observation results, pretreatment with L-ABH significantly inhibited macrophage migration mediated with RPE which was induced with TNFα. Therefore, in laser-damaged CNV models, intravenous injection of L-ABH inhibited CNV by inhibiting RPE from producing VEGF and MCP-1.

Conclusion

Intravenous injection of L-aspartic acid β-hydroxamate, by inhibiting RPE from producing VEGF and MCP-1, thus plays a role of inhibiting choroidal neovascularization in laser-damaged animal models.

It should be understood to persons skilled in the art that the present invention has been described following the above detailed description, while the inventive ideas of the present invention were not restricted to the present invention, and any variations employing the ideas of the present invention should be included in the protection scope of the claims.

The above descriptions represent various embodiments of the present invention, the protection scope of which should not be limited by the above embodiments, and all technical schemes within the spirit of the present invention all belong to the protection scope of the present invention. It should be noted to persons of ordinary skills in the art that several improvements and modifications without departing from the principle of the present invention also should be deemed as the protection scope of the present invention.

What is claimed is:

1. A method of inhibiting or treating choroidal neovascularization, wherein the method comprises administering an injectable preparation of L-aspartic acid β-hydroxamate to a patient suffering from choroidal neovascularization, wherein a first dosage injected is 6 mg/kg by weight of the treated patient, and a second dosage injected is 3 mg/kg.

2. The method of inhibiting or treating choroidal neovascularization according to claim 1, wherein the injection is an intravenous injection.

3. The method of inhibiting or treating choroidal neovascularization according to claim 1, wherein the second dosage is injected 3 days after the first dosage.

\* \* \* \* \*